United States Patent [19]

Imamura et al.

[11] Patent Number: 5,089,393
[45] Date of Patent: Feb. 18, 1992

[54] ASSAY METHOD FOR PHOSPHATIDYL ETHANOLAMINE

[75] Inventors: Shigeyuki Imamura; Hideo Misaki, both of Shizuoka, Japan

[73] Assignee: Toyo Jozo Kabushiki Kaisha, Shizuoka, Japan

[21] Appl. No.: 176,235

[22] Filed: Mar. 31, 1988

Related U.S. Application Data

[60] Division of Ser. No. 865,584, May 21, 1986, Pat. No. 4,788,147, which is a continuation of Ser. No. 675,241, Nov. 26, 1984, abandoned, which is a continuation of Ser. No. 447,539, Dec. 7, 1982, abandoned.

[30] Foreign Application Priority Data

Dec. 7, 1981 [JP] Japan ................. 56-197554

[51] Int. Cl.$^5$ ............................................. C12N 9/06
[52] U.S. Cl. ...................................... 435/28; 435/189; 435/191
[58] Field of Search .................. 435/11, 14, 18, 25, 435/189, 191, 19, 28; 436/7

[56] References Cited

FOREIGN PATENT DOCUMENTS

80/01081  5/1980  PCT Int'l Appl. ................. 435/28

OTHER PUBLICATIONS

Taki et al., "Phospholipase D from Rat Brain" in Methods in Enzymology, Ed. by Lowenstein (N.Y. Acad Press, 1981), vol. 71, 746–50.
Narrod et al., "Metabolism of Ethanolamine", Journal of Bio. Chem., vol. 239, No. 7 (1964), pp. 2189–2193.

Primary Examiner—Christine Nucker
Assistant Examiner—Laurie A. Scheiner
Attorney, Agent, or Firm—Young & Thompson

[57] ABSTRACT

Ethanolamine in a sample can be assayed by treating the sample with ethanolamine oxidase, thereby to catalyze a reaction-consuming ethanolamine, oxygen and water, and forming glycolaldehyde, ammonia and hydrogen peroxide. The amount of consumed oxygen or the amount of generated ammonia or hydrogen peroxide is then determined, as a measure of the ethanolamine that was originally the sample. The ethanolamine can appear in the sample as such, or can be liberated simultaneously with or prior to the catalysis reaction, from an ethanolamine derivative, e.g. phosphatidyl ethanolamine by the action of phospholipase D. Ethanolamine oxidase can be produced from Bacillus sp. B-0783 FERM-P No. 5798 in a conventional culture medium, preferably by submerged aeration liquid culturation.

2 Claims, 3 Drawing Sheets 10 mM ETHANOLAMINE 10 mM PHOSPHOLIPID

ASSAY METHOD FOR PHOSPHATIDYL ETHANOLAMINE

This application is a continuation, division of application Ser. No. 865,584, filed May 21, 1986, which is a continuation of Ser. No. 675,241 filed Nov. 26, 1984, which is a continuation of Ser. No. 447,539 filed Dec. 7, 1982.

This invention relates to an assay method for ethanolamine. More particularly, the present invention concerns an assay method for ethanolamine in a sample, which comprises treating a sample containing ethanolamine with ethanolamine oxidase, which catalyzes a reaction consuming ethanolamine, oxygen and water and liberating glycolaldehyde, ammonia and hydrogen peroxide, then measuring the amount of consumed oxygen or generated ammonia or hydrogen peroxide.

In clinical examination, serum phospholipids, of which 95% are phospholipids of choline derivatives, can be assayed by an enzymatic method using phospholipase D and choline oxidase. However, the remaining approximately 5% of phospholipids could not be assayed due to their non-reactivity in the presence of choline oxidase. These unassayable phospholipids are phospholipids of ethanolamine derivatives.

We have found that Bacillus sp. B-0783 FERM-P No. 5798 produces ethanolamine oxidase which catalyses a reaction of ethanolamine, oxygen and water to glycolaldehyde, ammonia and hydrogen peroxide. We have also found that ethanolamine can be assayed by treating a sample containing ethanolamine with ethanolamine oxidase, and measuring the amount of consumed oxygen or liberated ammonia or hydrogen peroxide. Furthermore, we have found that by the use of this method, phospholipids of ethanolamine derivatives can also be assayed by treating the said derivatives with phospholipase D to liberate ethanolamine, and simultaneously or subsequently treating the liberated ethanolamine with ethanolamine oxidase, then measuring the thus-consumed oxygen or the thus-liberated ammonia or hydrogen peroxide.

An object of the present invention is to provide an assay method for ethanolamine in a sample containing the same.

Another object of the present invention is to provide an assay method comprising treating a liquid sample containing ethanolamine with ethanolamine oxidase, which is an enzyme which catalyzes a reaction consuming ethanolamine, oxygen and water and generating glycolaldehyde, ammonia and hydrogen peroxide, and measuring the amount of consumed oxygen or liberated ammonia or hydrogen peroxide.

A further object of the present invention is to provide a simple and exact assay method for ethanolamine in a sample.

A still further object of the present invention is to provide a method for the quantitative determination of specific ethanolamine derivatives in samples containing various phospholipids such as phospholipids of ethanolamine derivatives and choline derivatives.

The ethanolamine can be ethanolamine liberated from ethanolamine derivatives, or ethanolamine itself.

Examples of ethanolamine derivatives which liberate ethanolamine are physiological phospholipid phosphatidyl ethanolamines and ethanolamine derivatives derived from chemical syntheses on the hydroxyl group or amino group of ethanolamine. These derivatives are all those which can liberate ethanolamine. For example, phosphatidyl ethanolamine liberates ethanolamine upon being treated with phospholipase D. Phospholipase D is an enzyme catalyzing a reaction which generates phosphatidic acid and choline from equimolar quantities of lecithin and water.

Phospholipase D is preferably obtained from microbial origin. For example, it can be obtained from cultured broth of *Streptomyces hachijoensis* A-1143 FERM-P No. 1329, *Streptomyces chromofuscus* A-0848 FERM-P No. 3519 or as commercially available phospholipase D.

The amount of phospholipase D used should be sufficient to liberate ethanolamine, for example more than 0.1 U/ml of enzymatic activity, preferably 2-50 U/ml. The reaction proceeds in a weakly acidic or alkaline buffer solution such as Tris-HCl buffer, citrate buffer, borate buffer, Pipes-NaOH buffer or imidazole buffer, for more than 5 minutes, preferably 10-20 minutes at 37° C.

Other ethanolamine derivatives can be split at the hydroxyl or amino positions to liberate ethanolamine by suitable enzymes or chemical reagents.

The thus-liberated ethanolamine or originally existing ethanolamine is treated by ethanolamine oxidase which catalyzes a reaction that consumes ethanolamine, oxygen and water to form glycolaldehyde, ammonia and hydrogen peroxide. Ethanolamine oxidase can be obtained, for example, from cultured broth of Bacillus sp. B-0783 FERM-P No. 5798 (Jap. Pat. Appln. No. 56-91937) or a microbial strain belonging to genus Arthrobacter. [J. Biol. Chem., 239, 2189 (1964)]. The enzyme can preferably be purified, or modified to the form of an immobilized enzyme.

The taxonomical properties of Bacillus sp. B-0783 are as follows:

A. Growth on various media:
1. Bouillon agar plate (30° C., 18 hours culture): Round, planar colony, smooth edges, graywish white - pale yellowish gray. No soluble pigment formation.
2. Bouillon agar slant (30° C., 18 hours culture): Filamentous good growth, grayish white - pale yellowish gray. No soluble pigment formation.
3. Bouillon broth (30° C., 32 hours culture): Weak growth, precipitation.

B. Microscopic observation: Cultured on nutrient agar medium at 30° C. for 18 hours.
1. Form and size of cells: Single, double or short-linkage, round-edged bacilli, $1.0-1.5 \times 2.0-5.0$ μm.
2. Polymorphism: none.
3. Mobility and flagella: Peritrichous, mobile.
4. Spore (form, position, size): Spore, oospherical or elliptical, forms on edges or near edges of cells, spindle spores.

C. Physiological properties:

| | |
|---|---|
| Nitrate reduction | + |
| Denitrate reaction | − |
| MR test | − |
| VP test | − |
| Indole formation | − |
| $H_2S$ | − |
| Gelatin hydrolysis | + (weak) |
| Starch hydrolysis | − |
| Citrate utilization | |
| Simons medium | − |
| Chrystensen medium | − |
| Nitrate utilization | + |
| Ammonium slat utilization | − |

-continued

| | |
|---|---|
| Pigment formation | − |
| Oxidase | + |
| Catalase | + |
| Urease | . |
| SSR medium | − |
| Chrystensen medium | − |
| Growth conditions: | |
| pH: optimum pH | 6.5–8.0 |
| growth pH | 5.0–9.0 |
| temperature: | |
| optimum temperature | 25–37° C. |
| growth temperature | 10–42° C. |
| Nature: aerobic | |
| OF test (Hugh Leifson medium) | Al (alkaline) |
| OF test (modified medium) | Al (alkaline) |
| Esculin decomposition | − |
| Cellulose decomposition | − |
| Gram's stain | + |
| Acid fast stain | − |

| Acid and gas formation | | |
|---|---|---|
| | Acid | Gas |
| adnitol | − | − |
| L(+)arabinose | − | − |
| cellobiose | − | − |
| dulcitol | − | − |
| meso-erythritol | + | − |
| D(−)fructose | − | − |
| fucose | − | − |
| D(+)galactose | − | − |
| D(+)glucose | − | − |
| glycerol | − | − |
| inositol | − | − |
| inulin | − | − |
| lactose | − | − |
| maltose | − | − |
| D-mannitol | − | − |
| D-mannose | − | − |
| melezitose | − | − |
| melibiose | − | − |
| raffinose | − | − |
| L(+)rhamnose | − | − |
| salicin | − | − |
| L-sorbose | − | − |
| sorbitol | − | − |
| starch | − | − |
| saccharose | − | − |
| trehalose | − | − |
| D-xylose | − | − |
| GC content of DNA (Tm method) | 37.3% | |

Considering the above taxonomical properties, the strain B-0783, being a Gram positive and spore forming bacillus, is confirmed as belonging to genus Bacillus by consulting Bergey's Manual of Determinative Bacteriology, 8th Ed. (1974). Furthermore, the various taxonomical characteristics are compared according to a description of the above manual and "The Genus Bacillus", in Agricultural Handbook, p. 427; and as the identical characteristics were not found, so this strain is referred to as Bacillus sp. B-0783. The strain has been deposited in the Fermentation Research Institute, Agency of Technological Science and Industry, M.I.T.I., Japan as FERM-P No. 5798.

Ethanolamine oxidase can be obtained by culturing the above ethanolamine-producing Bacillus sp. B-0783 in a conventional medium. Solid or liquid medium can be used; however, submerged aeration liquid culture is preferable for industrial production.

Conventional nutrient media can be selected for enzyme production. As for carbon sources, assimilable carbon sources such as glucose, sucrose, lactose, maltose, starch, dextrin, molasses or glycerin can be used. Assimilable nitrogen sources such as corn steep liquor, soybean powder, cotton seed powder, wheat gluten, peptone, meat extract, yeast extract or casein hydrolyzate can be used. Various salts such as sodium chloride, potassium chloride, potassium phosphate or magnesium sulfate are optionally used. The addition of an alkylamine such as ethanolamine or propionylamine to the medium at a concentration of 0.1 to 1% induces the production of ethanolamine oxidase.

The culturing temperature can be selected within the ranges for the growth of microorganisms and the production of enzymes, and is preferably 26°–33° C., most preferably 30° C. The culturing time can be selected depending on conditions and is usually 15–25 hours. Culturing is conducted at 200–400 rpm with aeration and should naturally be terminated when ethanolamine oxidase production is substantially complete.

Examples of methods for the extraction of ethanolamine oxidase from the cultured mass are as follows:

Since the ethanolamine oxidase is an endo-enzyme, the cultured mass is filtered or centrifuged and the bacterial cells are disrupted by mechanical means such as a French-press or by glass beads treatment or by enzymatic means such as lysozyme. Furthermore, surface active agents such as Triton X-100 (trademark) or Adekatol SO-120 (trademark) are optionally added. The thus-obtained crude ethanolamine oxidase is purified by conventional isolation and purification methods for enzymes. For example, fractional precipitation with acetone, ethanol or isopropanol and salting out with ammonium sulfate are preferably used. Further purification can be achieved by, for example, ion exchange chromatography using DEAE-Sephadex, DEAE-Sephalose, DEAE-cellulose, CM-cellulose, or CM-Sephadex, or gel filtration chromatography using Sephadex G-200, Sepharose CL-6B or Sephacryl S-200, and lyophilization.

Figure 1:
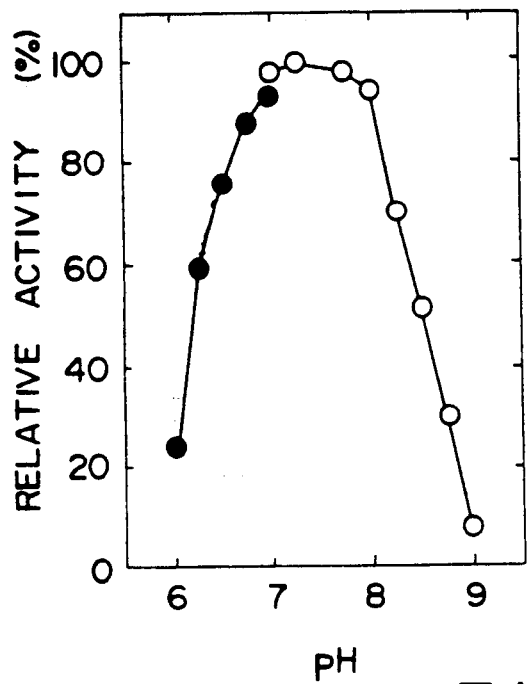
FIG. 1 is the optimum pH curve of ethanolamine oxidase.

The assay method and biochemical properties of ethanolamine oxidase obtained from Bacillus sp. B-0783 are as follows:

(1) Assay method:

| | |
|---|---|
| 0.2 M Tris-HCl buffer (pH 8.0) | 0.1 ml |
| 0.3% 4-aminoantipyrine | 0.02 ml |
| 3 mM N,N-diethyl-m-toluidine | 0.05 ml |
| (45 U/ml) peroxidase | 0.05 ml |
| 0.1 M ethanolamine | 0.05 ml |
| distilled water | 0.18 ml |
| Total | 0.45 ml |

The above mixture (0.45 ml) is preincubated at 37° C. for 2 minutes, enzyme solution (50 μl) is added thereto and the mixture is incubated at 37° C. for 10 minutes.

The reaction is stopped by adding ethanol (2.5 ml) and the extent of the reaction is colorimetrically measured at 550 nm.

A unit (1 unit, 1 U) of enzyme activity is defined as the activity of enzyme which generates 1 μmole of hydrogen peroxide per minute.

The potency of the enzyme is calculated by the following equation:

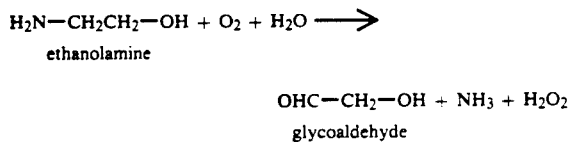

$$\text{Enzyme activity (U/ml)} = \Delta A_{550} \times 0.25 \times \frac{1000}{50} \times \frac{1}{10}$$

wherein $\Delta A_{550}$ is the absorption value at 550 nm.

(2) Enzyme action:

The oxidation of one mole of ethanolamine consumes one mole of oxygen and one mole of water and liberates one mole of glycolaldehyde, one mole of ammonia and one mole of hydrogen peroxide; thus:

$$H_2N-CH_2CH_2-OH + O_2 + H_2O \longrightarrow$$
ethanolamine $$OHC-CH_2-OH + NH_3 + H_2O_2$$
glycoaldehyde (3) Substrate specificity:

| Substrate | Activity (%) |
|---|---|
| ethanolamine | 100 |
| 1-amino-2-propanol | 26.5 |
| 3-amino-2-propanol | 357 |
| 3-amino-1,2-propanediol | 0 |
| diethanolamine | 0 |
| triethanolamine | 0 |
| choline | 0 |

(4) Optimum pH: pH 7-7.5
Shown in FIG. 1.

| | |
|---|---|
| pH 6-7: | phosphate buffer, |
| pH 7-9: | Tris-HCl buffer. |

Figure 2:
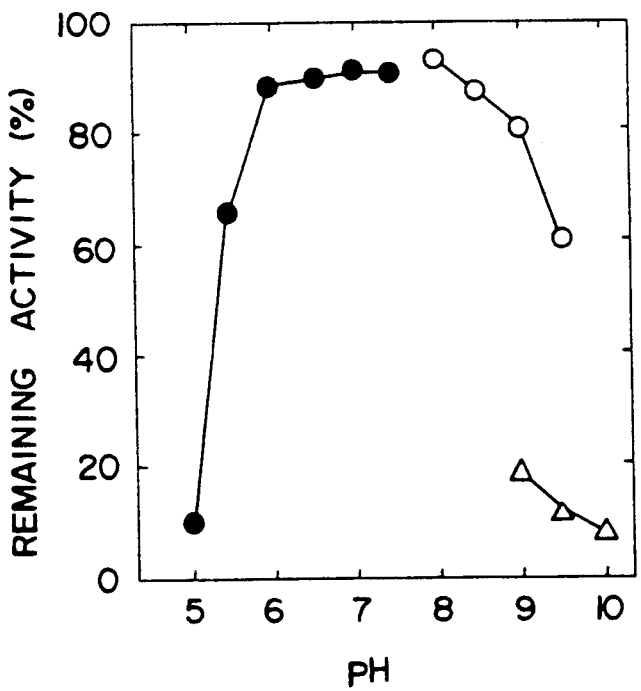
FIG. 2 is the pH-stability curve of ethanolamine oxidase.

(5) pH-stability:

Enzyme solution is added to buffers (100 mM) of various pH, (pH 5-7.5: dimethylglutarate buffer, pH 8-9.5: Tris-HCl buffer, pH 9-10: glycine-NaOH buffer) at 60° C. for 15 minutes and the remaining activity is assayed. The results are shown in FIG. 2, wherein the stable pH is pH 6-8.

Figure 3:
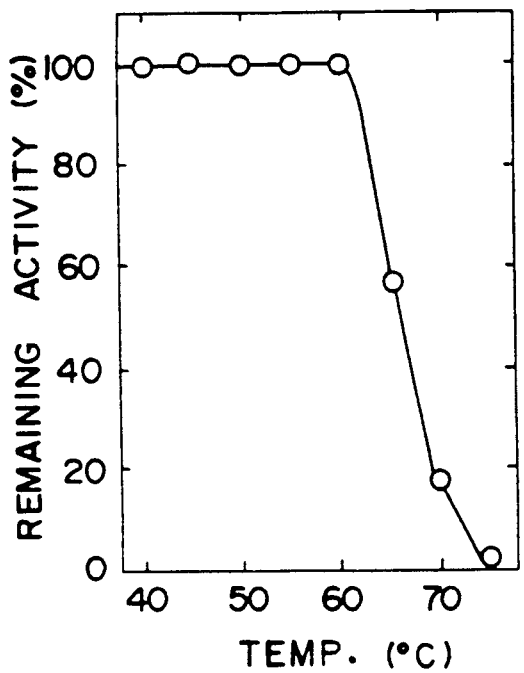
FIG. 3 is the heat-stability curve of ethanolamine oxidase.

(6) Heat stability:

The enzyme solution (2.5 U/ml) in 10 mM Tris-HCl buffer (pH 8.0) is treated for 10 minutes at 40°-75° C., and the remaining activity is assayed. The results are shown in FIG. 3, wherein the enzyme is stable up to 60° C.

(7) Isoelectric point:

Approximately pH 4.60 (assayed by isoelectric focusing using carrier ampholite).

(8) Effect of metal ions and EDTA:

| Metal ion, EDTA | Activity (%) |
|---|---|
| Control (no addition) | 100 |
| 1 mM CaCl$_2$ | 35 |
| 1 mM MgCl$_2$ | 110 |
| 1 mM BaCl$_2$ | 58 |
| 1 mM MnCl$_2$ | 52 |

-continued

| Metal ion, EDTA | Activity (%) |
|---|---|
| 1 mM EDTA | 122 |
| 100 mM KCl | 97 |
| 100 mM NaCl | 64 |
| 100 mM NH$_4$Cl | 61 |
| 100 mM LiCl | 36 |

(9) Effect of surface active agents:

| Surface active agents | Activity (%) |
|---|---|
| Control (no addition) | 100 |
| 0.1% Triton X-100 | 98 |
| 0.1% Adekatol SO-145 | 90 |
| 0.1% sodium deoxycholate | 83 |
| 0.1% sodium lauryl benzene sulfate | 29 |
| 0.1% sodium lauryl sulfate | 26 |

The amount of ethanolamine oxidase used in an assay is at least 0.1 U/ml, preferably at least 0.5 U/ml, at 37° C. for at least one minute, preferably at least 5 minutes. Ethanolamine oxidase can be used with phospholipase D simultaneously or subsequently.

At the end of the reaction, the consumed oxygen or liberated ammonia or hydrogen peroxide is measured. The corresponding electrode such as an oxygen electrode, ammonia electrode, or hydrogen peroxide electrode is used for detection, or an immobilized enzyme electrode of ethanolamine oxidase or ethanolamine oxidase-phospholipase D is used. For the assay with an electrode, electric current changes corresponding to the amount of component to be detected are measured as a quantitative assay, and the said electric current is measured through the interface by the end-point method, the rate assay method or the quadratic differential method, and recorded in a recorder.

Colorimetric assay can be used for the quantitative determination of hydrogen peroxide. For example, one or more coloring reagents or fluorescents which change color in the presence of hydrogen peroxide, can be used. Examples of the coloring reagent are peroxidases such as horseradish peroxidase and dye precursors such as the combination of an electron acceptor and a phenolic compound.

Examples of the electron acceptor are 4-aminoantipyrine, 2-hydrozinobenzothiazole, 3-methyl-4-benzothiazole hydrozine or 2-aminobenzothiazole. Examples of the phenolic compound are phenol, 3-methyl-N-ethyl-N-(β-hydroxyethyl) aniline, 3,5-xylenol, N-N-dimethylaniline or N,N-diethylaniline. Examples of the fluorescents are conventional bis (2,4,6-trichlorophenol) oxalate, phenylthiohydantoine, homovanillic acid, 4-hydroxyphenylacetic acid, vanillylamine, 3-methylthiramine, fluorolethinic acid, hordenine, luminol monoanion, lucigenin or wafin. These fluorescents are optionally used together with an electron acceptor and peroxidase. The amount of enzyme reagent and dye precursor is not limited and is usually at least 0.05 unit for peroxidase in a single test, preferably 0.1-500 units, of at least 0.1 mM concentration in distilled water or weak acidic or alkaline buffer for the electron acceptor and phenolic compound. These reagents can be used separately or together with the above phospholipase C or D and ethanolamine oxidase. Furthermore, these reagents can be provided as quantitative assay components in lyophilized form or laminate form on filter paper or film.

The assay method of the present invention is useful for the specific quantitative determination of phosphatidylethanolamine in serum phospholipids.

Clinical examination in combination with the assay of choline derivatives and ethanolamine derivatives can provide fractional determinations of phospholipids of ethanolamine derivatives and phospholipids of choline derivatives.

The following examples illustrate the present invention but are not to be construed as limiting.

EXAMPLE 1

| | |
|---|---|
| 0.2 M Tris-HCl buffer (pH 8.0) | 0.5 ml |
| 0.3% 4-aminoantipyrine | 0.3 ml |
| 0.2% phenol | 0.3 ml |
| peroxidase (45 U/ml, Sigma Chem.) | 0.1 ml |
| ethanolamine oxidase (6 U/ml, obtained from Example 6) | 0.1 ml |
| 0.5% NaN$_3$ | 0.3 ml |
| 5% Triton X-100 | 0.2 ml |
| 10 mM MgCl$_2$ | 0.3 ml |
| distilled water | 0.9 ml |
| Total | 3.0 ml |

Ethanolamine solution (5-25 μl) was added to the above reaction mixture (3.0 ml), and the mixture was incubated at 37° C. for 20 minutes and colorimetrically measured at 500 nm.

Figure 4:
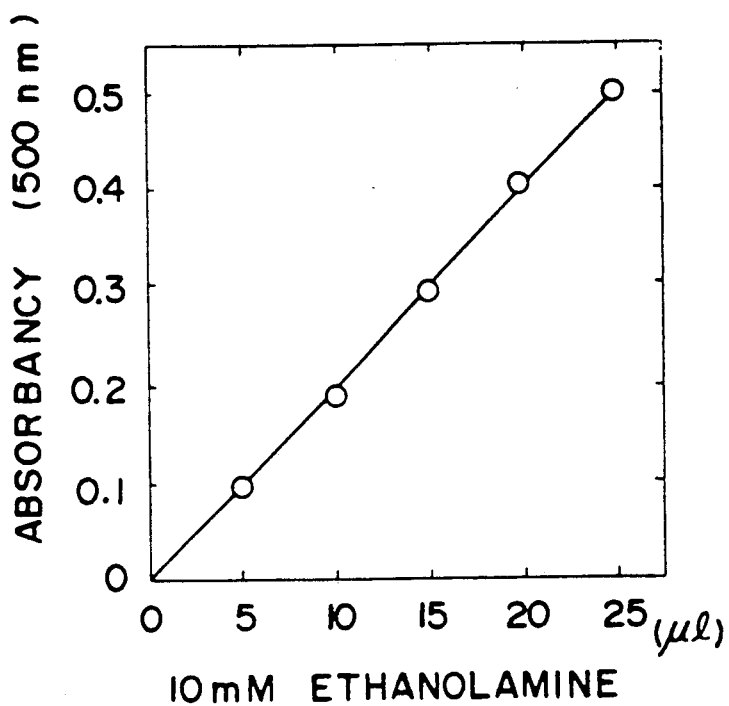
FIG. 4 is the standard absorbency curve of ethanolamine.

The results are shown in FIG. 4, wherein an accurate standard absorbency curve of ethanolamine is obtained.

The ethanolamine was then replaced by a reaction mixture of phosphatidyl ethanolamine treated with phospholipase D (containing Triton X-100 and MgCl$_2$) at 37° C. for 10 minutes to assay phosphatidyl ethanolamine.

EXAMPLE 2

| | |
|---|---|
| 0.2 M Tris-HCl buffer (pH 8.0) | 0.5 ml |
| 0.3% 4-aminoantipyrine | 0.3 ml |
| 0.2% phehol | 0.3 ml |
| peroxidase (45 U/ml) | 0.1 ml |
| ethanolamine oxidase (6 U/ml) | 0.1 ml |
| 0.5% NaN$_3$ | 0.3 ml |
| 5% Triton X-100 | 0.2 ml |
| 10 mM Mg Cl$_2$ | 0.3 ml |
| phospholipase D (20 U/ml; Toyo Jozo Co.) | 0.1 ml |
| distilled water | 0.8 ml |
| Total | 3.0 ml |

A 10 mM phospholipid emulsion (5-25 μl) was added to the above reaction mixture (3 ml), and the mixture was incubated at 37° C. for 20 minutes and colorimetrically measured at 500 nm.

Figure 5:
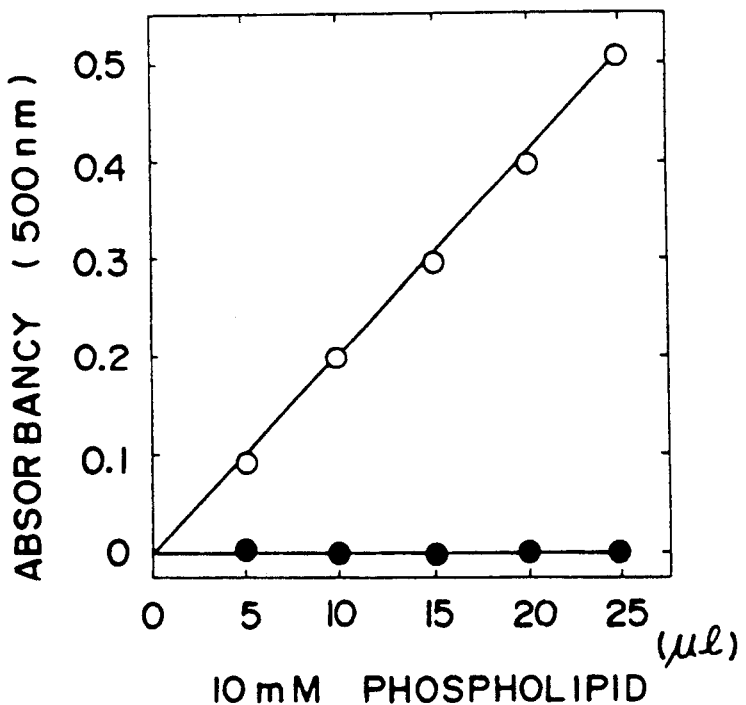
FIG. 5 is the quantitative assay curve of phosphatidyl ethanolamine by determining the amount of generated hydrogen peroxide.

The results are shown in FIG. 5, wherein o—o; phosphatidylamine and o—o; lecithin were used as the phospholipids. In the figure, the enzyme could not act on lecithin and phosphatidyl ethanolamine could be assayed exactly.

EXAMPLE 3

| | |
|---|---|
| 0.2 M Tris-HCl buffer (pH 7.5) | 0.2 ml |
| ethanolamine oxidase (6 U/ml) | 0.1 ml |
| distilled water | 0.7 ml |
| Total | 1.0 ml |

2 mM ethanolamine (5-25 μl) was added to the above reaction mixture (1 ml), and the mixture was incubated at 37° C. for 10 minutes and consumed oxygen was measured by an oxygen electrode (product of Ishikawa Seisakusho).

Figure 6:
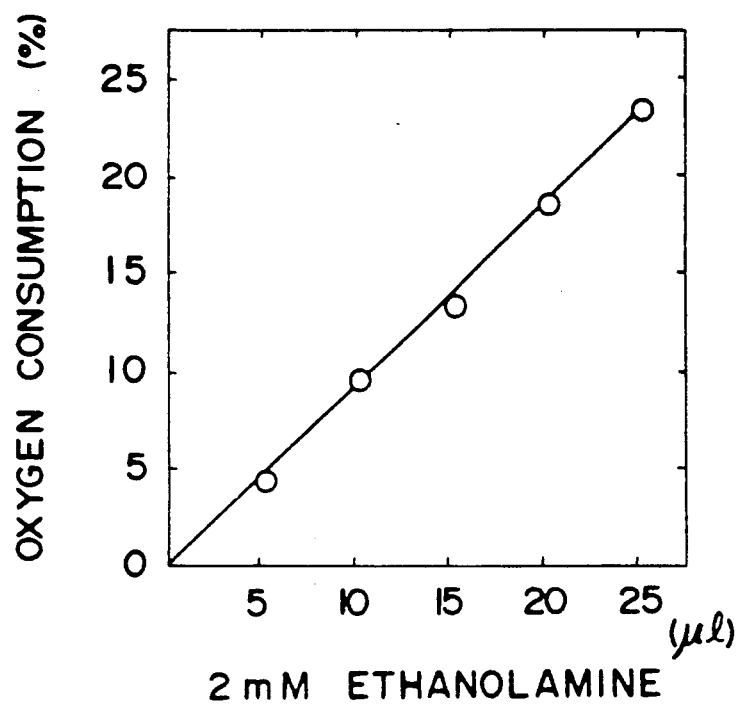
FIG. 6 is the quantitative assay curve of ethanolamine by determining the amount of consumed oxygen.

The results are shown in FIG. 6, wherein an exact linear standard curve of oxygen consumption can be observed, and the said linearity can be observed at least down to 0.05 μmole of ethanolamine.

Phosphatidyl ethanolamine can thus be quantitatively determined by treatment with phospholipase D (containing Triton X-100 and MgCl$_2$).

EXAMPLE 4

| | |
|---|---|
| 0.2 M Tris-HCl buffer (pH 7.5) | 0.5 ml |
| ethanolamine oxidase (6 U/ml) | 0.1 ml |
| 10 mM MgCl$_2$ | 0.2 ml |
| 5% Triton X-100 | 0.1 ml |
| phospholipase D (20 U/ml) | 0.1 ml |
| distilled water | 1.0 ml |
| Total | 2.0 ml |

2 mM phosphatidyl ethanolamine (5-25 μl) was added to the above reaction mixture (2.0 ml) and the mixture was incubated at 37° C. for 10 minutes. The amount of generated hydrogen peroxide was measured by using a hydrogen peroxide electrode (YSI Co., oxidase meter) and as little as 0.05 μmole of phosphatidyl ethanolamine could be linearly assayed.

The above hydrogen peroxide electrode can be replaced by an oxygen electrode by which the amount of consumed oxygen can be measured.

EXAMPLE 5

| | |
|---|---|
| 0.2 M Tris-HCl buffer (pH 7.5) | 0.2 ml |
| ethanolamine oxidase (6 U/ml) | 0.1 ml |
| 5% Triton X-100 | 0.1 ml |
| distilled water | 2.6 ml |
| Total | 3.0 ml |

2.5 mM ethanolamine (10-50 μl) was added to the above reaction mixture (3.0 ml), and the mixture was incubated at 37° C. for 15 minutes; thereafter 5 N-NaOH (50 μl) was added, and the amount of liberated ammonia was measured by using an ammonia electrode (product of Ishikawa Works).

Figure 7:
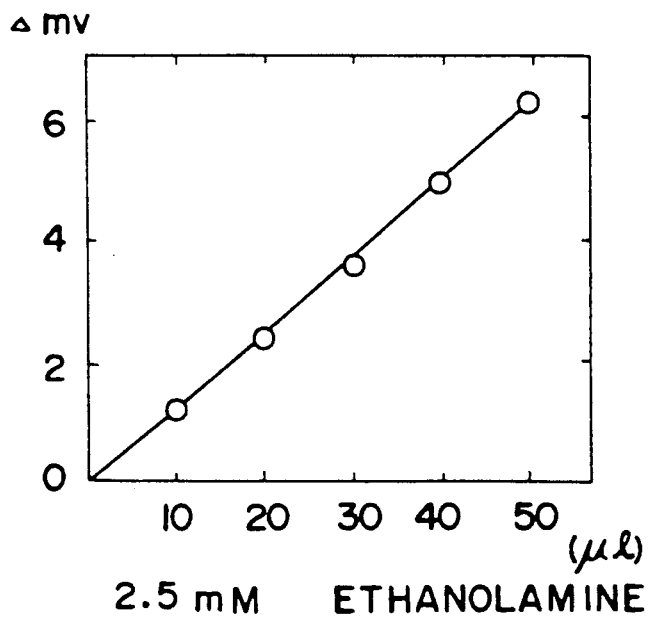
FIG. 7 is the quantitative assay curve of ethanolamine by use of an ammonia electrode.

The results are shown in FIG. 7, wherein as little as 0.025 μmole of ethanolamine can be linearly assayed.

In place of ethanolamine, phosphatidyl ethanolamine, treated with phospholipase D (containing Triton X-100 and MgCl$_2$) at 37° C. for 10 minutes, can be assayed.

EXAMPLE 6

An aqueous medium (20 lit., pH 6.8) comprising peptone 1.5%, powdered yeast extract 0.5%, KCl 0.2%, NaCl 0.1%, K$_2$HPO$_4$ 0.1%, MgSO$_4$ 0.1%, silicone KM-72 0.05% and ethanolamine 0.5%, in a 20 lit. jar-fermenter, was sterilized at 120° C. for 20 mins. A seed culture of Bacillus sp. B-0783 FERM-P No. 5798 cultured in a rotary shaker at 30° C. for 20 hours in the same medium (500 ml) was inoculated into the above medium and the mixture was cultured at 30° C. for 17 hours at 3000 rpm, with 20 lit./minute aeration. The cultured broth was centrifuged at 5000 rpm for 20 minutes to obtain bacterial cells. The cells suspended in lysozyme (Eizai Co., 500 mg) solution (2 lit.) in a 10 mM phosphate buffer (pH 7.0) were treated at 37° C. for 2 hours to obtain a crude enzyme solution (1700 ml, 0.2 U/ml). Cold acetone (850 ml) was added thereto and the precipitate was removed by centrifugation (5000 rpm, 10 minutes). Then cold acetone (1200 ml) was added to the supernatant solution, and the precipitate was collected by centrifugation at 0° C., at 5000 rpm for 10 minutes.

The precipitate was dissolved in 0.1 mM Tris-HCl buffer (pH 8.0, 100 ml) containing 0.5 M KCl and dialyzed with a cellophane tube. The dialyzate was lyophilized to obtain ethanolamine oxidase powder (0.1 U/mg, 3.2 g).

The powder (1.0 g) dissolved in 10 mM Tris-HCl buffer (pH 8.0, 15 ml) was charged on a column (2.5×21 cm) of DEAE-Sepharose CL-6B (Pharmacia Co.) equilibrated with the same buffer and washed with the same buffer (500 ml). Gradient elution with 200 ml of 10 mM Tris-HCl buffer (pH 8.0) and the same buffer containing 0.5 M KCl was performed. Each 10 ml fraction was fractionated and the active fractions Nos. 56–66 were collected. The combined active fractions were dialyzed against 10 mM-Tris HCl buffer (pH 8.0) and lyophilized to obtain ethanolamine oxidase powder (0.7 U/ml, 110 mg).

What is claimed is:

1. An assay method for phosphatidyl ethanolamine in a sample, which comprises treating a sample containing phosphatidyl ethanolamine in a single step with a mixture of phospholiapse D an ethanolamine oxidase whose optimum pH is 7–7.5 and whose pH stability is pH 6–8, in a weakly alkaline buffer solution, said ethanolamine oxidase being obtained by culturing Bacillus sp. B-0783 FERM-P No. 5798, said phospholipase D liberating ethanolamine from said phosphatidyl ethanolamine and said oxidase catalyzing a reaction consuming ethanolamine, oxygen and water to form glycolaldehyde, ammonia and hydrogen peroxide, and measuring the amount of consumed oxygen or generated ammonia or hydrogen peroxide in the reaction system.

2. Ethanolamine oxidase obtained from the microorganism Bacillus sp. B-0783 FERM-P No. 5798.

* * * * *